United States Patent
Bergersen

(10) Patent No.: US 7,234,933 B2
(45) Date of Patent: Jun. 26, 2007

(54) DENTAL APPLIANCE AND METHOD FOR REDUCING AN AMOUNT OF PATIENT COOPERATION

(75) Inventor: Earl O. Bergersen, Dorado, PR (US)

(73) Assignee: Ortho-Tain, Inc., Winnetka, IL (US)

( * ) Notice: Subject to any disclaimer, the term of this patent is extended or adjusted under 35 U.S.C. 154(b) by 107 days.

(21) Appl. No.: 10/760,604

(22) Filed: Jan. 20, 2004

(65) Prior Publication Data

US 2004/0152032 A1 Aug. 5, 2004

Related U.S. Application Data

(60) Provisional application No. 60/441,619, filed on Jan. 21, 2003.

(51) Int. Cl.
*A61C 3/00* (2006.01)

(52) U.S. Cl. ............................................ 433/6; 433/24

(58) Field of Classification Search .................... 433/6, 433/24

See application file for complete search history.

(56) References Cited

U.S. PATENT DOCUMENTS

| | | |
|---|---|---|
| 3,510,946 A | 5/1970 | Kesling |
| 3,724,075 A | 4/1973 | Kesling |
| 3,837,081 A | 9/1974 | Kesling |
| 3,950,851 A * | 4/1976 | Bergersen ...................... 433/6 |
| 4,015,032 A | 3/1977 | Hanna |
| 4,073,061 A | 2/1978 | Bergersen |
| 4,139,944 A | 2/1979 | Bergersen |
| 4,370,129 A | 1/1983 | Huge |
| 4,371,336 A | 2/1983 | Hilleman |
| 4,396,373 A | 8/1983 | Dellinger |
| 4,448,735 A * | 5/1984 | Huge ........................... 264/16 |
| 4,568,280 A | 2/1986 | Ahlin |
| 4,580,975 A * | 4/1986 | Schrems et al. ................ 433/6 |
| 4,591,341 A * | 5/1986 | Andrews ....................... 433/6 |

(Continued)

FOREIGN PATENT DOCUMENTS

WO PCT/US98/08981 6/1998

(Continued)

*Primary Examiner*—Todd E. Manahan
(74) *Attorney, Agent, or Firm*—Patents + TMS, P.C.

(57) ABSTRACT

A dental appliance, a system and a method for treating malocclusions minimize cooperation by a patient for treating the malocclusions. A reline material is insertable between the appliance and one or more teeth of the patient. An internal surface of the appliance is roughened for receiving the reline material to increase retention of the appliance to one or more teeth of the patient. A hinge connects an upper half to a lower half to increase retention of the appliance to one or more teeth of the patient. The appliance maintains a lower jaw of the patient in a position with respect to an upper jaw of the patient. A lingual tab of the lower half maintains the lower jaw of the patient in the position with respect to the upper jaw of the patient. The appliance is made of one or more materials having varying stiffness and/or softness to increase retention of the appliance and/or to increase movement of one or more teeth of the patient. The upper half and/or the lower half is sized to allow eruption of one or more rear teeth of the patient without contacting the appliance.

74 Claims, 7 Drawing Sheets

U.S. PATENT DOCUMENTS

| | | | |
|---|---|---|---|
| 4,784,605 A | 11/1988 | Bergersen | |
| 4,793,803 A | 12/1988 | Martz | |
| 4,799,884 A | 1/1989 | Bergersen | |
| 4,830,612 A | 5/1989 | Bergersen | |
| 4,898,535 A * | 2/1990 | Bergersen | 433/6 |
| 4,919,612 A | 4/1990 | Bergersen | |
| 4,983,334 A | 1/1991 | Adell | |
| 4,986,751 A | 1/1991 | Bergersen | |
| 5,028,231 A | 7/1991 | Hall | |
| 5,037,294 A | 8/1991 | Bergersen | |
| 5,037,295 A | 8/1991 | Bergersen | |
| 5,042,506 A | 8/1991 | Liberati | |
| D323,215 S | 1/1992 | Bergersen | |
| 5,328,362 A | 7/1994 | Watson et al. | |
| 5,334,218 A | 8/1994 | Johnson | |
| 5,338,190 A | 8/1994 | Tregillis | |
| 5,645,420 A | 7/1997 | Bergersen | |
| 5,683,244 A * | 11/1997 | Truax | 433/6 |
| 5,779,470 A | 7/1998 | Kussick | |
| 5,807,100 A * | 9/1998 | Thornton | 433/48 |
| 5,814,074 A | 9/1998 | Branam | |
| 5,816,799 A | 10/1998 | Parker | |
| 5,876,199 A * | 3/1999 | Bergersen | 433/6 |
| 5,882,192 A | 3/1999 | Bergersen | |
| 5,911,576 A | 6/1999 | Ulrich et al. | |
| 5,975,893 A | 11/1999 | Chishti et al. | |
| 6,129,084 A | 10/2000 | Bergersen | |
| 6,183,248 B1 * | 2/2001 | Chishti et al. | 433/6 |
| 6,247,926 B1 * | 6/2001 | Thornton | 433/48 |
| 6,299,440 B1 | 10/2001 | Phan et al. | |
| 6,302,686 B1 | 10/2001 | Chott et al. | |
| 6,454,565 B2 | 9/2002 | Phan et al. | |
| 6,505,625 B1 | 1/2003 | Uenishi | |
| 6,572,372 B1 * | 6/2003 | Phan et al. | 433/6 |
| 6,582,225 B1 | 6/2003 | Bergersen | |
| 2002/0187451 A1 | 12/2002 | Phan et al. | |
| 2003/0224312 A1 | 12/2003 | Bergersen | |
| 2003/0224313 A1 | 12/2003 | Bergersen | |
| 2003/0224314 A1 | 12/2003 | Bergersen | |
| 2003/0225594 A1 | 12/2003 | Bergersen | |
| 2004/0052032 A1 | 3/2004 | Monden et al. | |
| 2004/0058295 A1 | 3/2004 | Bergersen | |
| 2005/0037311 A1 | 2/2005 | Bergersen | |

FOREIGN PATENT DOCUMENTS

| | | |
|---|---|---|
| WO | PCT/US03/16725 | 5/2003 |
| WO | PCT/US03/16733 | 5/2003 |
| WO | PCT/US03/17163 | 5/2003 |
| WO | PCT/US03/17196 | 5/2003 |
| WO | PCT/US03/29662 | 9/2003 |
| WO | PCT/US03/29667 | 9/2003 |

* cited by examiner

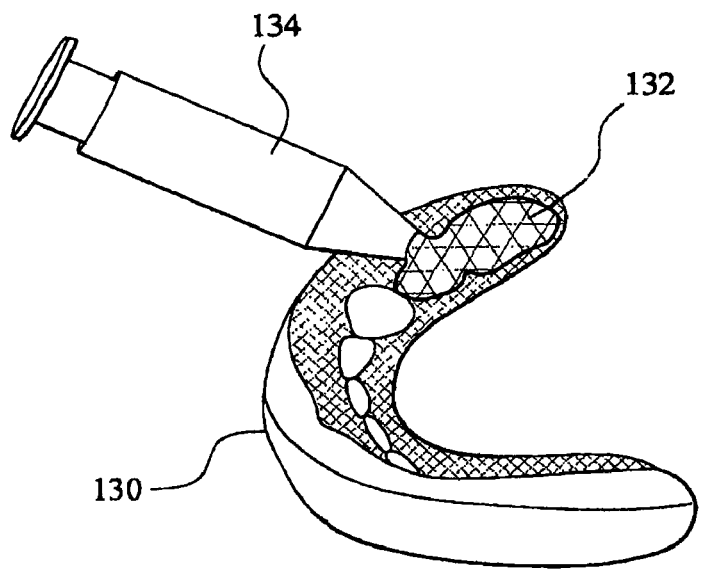
FIG. 10
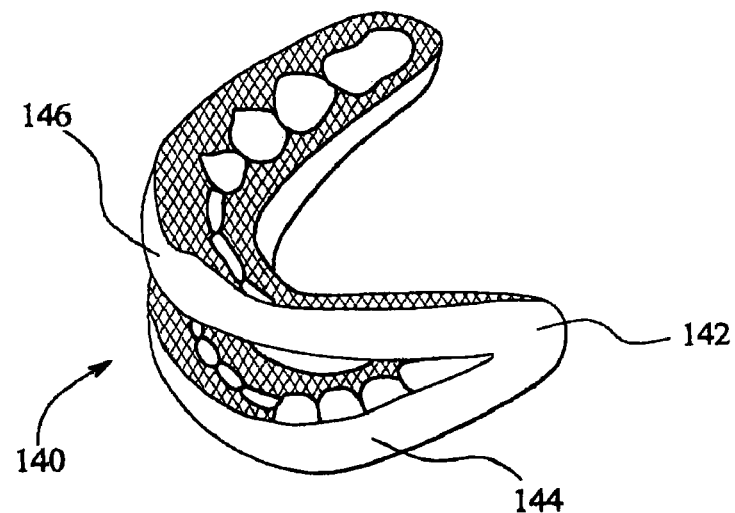
FIG. 11
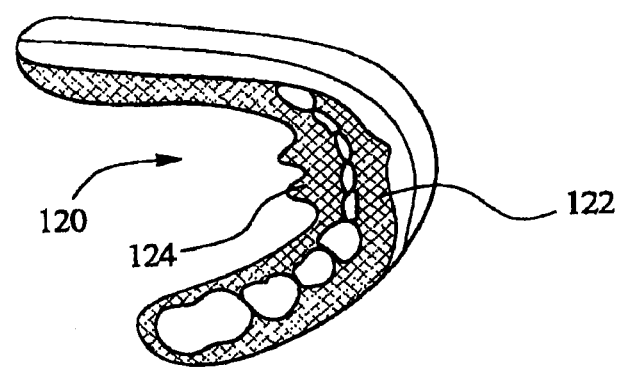

DENTAL APPLIANCE AND METHOD FOR REDUCING AN AMOUNT OF PATIENT COOPERATION

This application claims the benefit of U.S. Provisional Application Ser. No.: 60/441,619, filed Jan. 21, 2003.

BACKGROUND OF THE INVENTION

The present invention relates to a dental appliance and a system and a method for treating a malocclusion which may reduce an amount of cooperation required by the patient to treat the malocclusion. More specifically, the present invention relates to a dental appliance and a system and a method which may reduce an amount of exercise required by the patient, in conjunction with wearing of the dental appliance, to treat a malocclusion.

It is generally known to provide dental care to a patient. Typically, the patient may visit, for example, a dentist or other type of care provider at the office of the care provider. The dentist, for example, may then examine the patient using various techniques, including x-raying the area to be treated or other image-taking technique. The dentist may then provide the patient with a dental appliance to treat the condition of the patient.

In addition to the dental appliance, the dentist may provide the patient with instructions for exercises to perform while wearing the dental appliance. The exercises may cause, for example, the teeth to move toward a corrected position and may assist in treating the malocclusion.

However, the exercises may be tedious and/or time-consuming for the patient. In some cases, the exercises may cause pain to the patient. Accordingly, the patient may not be motivated to perform the exercises and may abandon them or otherwise not regularly perform the exercises to assist with and/or to correct the malocclusion. As a result, the malocclusion may not be corrected to completion. In other cases, the patient may not have time to perform the exercises because of conflicts such as, for example, employment, social and/or like conflicts or time constraints. Failure to perform the exercises may prevent or otherwise hinder complete correction of a malocclusion.

A need, therefore, exists for a dental appliance and a system and a method for reducing an amount of patient cooperation required for treatment of a malocclusion.

SUMMARY OF THE INVENTION

The present invention relates to a dental appliance and a system and a method for reducing an amount of cooperation required by the patient to treat a malocclusion using the dental appliance. In an embodiment, the dental appliance may be shaped to cause, for example, teeth of the user to erupt. Eruption of the teeth may reduce an amount of exercise a patient may perform in conjunction with wearing the dental appliance to treat the malocclusion. In another embodiment, the dental appliance may be constructed from a substance which causes the teeth of the user to adhere to the dental appliance. The dental appliance may then be prevented from slipping from the mouth which generally deters correction of the malocclusion. In another embodiment, a substance may be topically placed upon the teeth or within an inside surface of the dental appliance to increase the adherence of the dental appliance to the teeth of the user. In another embodiment, the dental appliance may have a hinge which prevents the dental appliance from slipping from the mouth of the patient. In another embodiment, a method is provided in which the patient may wear the dental appliance for short intervals of time while constantly clenching the dental appliance to treat a malocclusion. In another embodiment, a method is provided in which the patient reduces an amount of time the dental appliance is worn per day and extends an overall number of days the dental appliance is worn.

To this end, in an embodiment of the present invention, a dental appliance is provided which is placed in a mouth of a user wherein the user has teeth. The dental appliance has a generally U-shaped base having a length defined between a first end and a second end and having an occlusal surface wherein the occlusal surface contacts the teeth when the base is placed within the mouth wherein the base has an interior surface which substantially surrounds the occlusal surface. The dental appliance also has a reline material in contact with the interior surface wherein the reline material causes adhesion of the base to the teeth.

In an embodiment, the dental appliance has a solvent positioned between the reline material and the interior surface wherein the solvent enables the reline material to adhere to the interior surface.

In an embodiment, the interior surface is roughened.

In an embodiment, the dental appliance has the occlusal surface is flat.

In an embodiment, the dental appliance has a mark on the interior surface indicating an amount of the reline material in contact with the interior surface.

In an embodiment, the dental appliance has a socket formed within the interior surface wherein the socket is shaped to receive a tooth of the user.

In an embodiment, the base is constructed from a first material and a second material wherein the first material has a lesser degree of rigidity than the second material.

In an embodiment, the base is sized to contact at least one tooth but not all teeth when the base is placed within the mouth.

In an embodiment, the reline material adheres to the teeth.

In an embodiment, the base increases in rigidity from the first end to the second end.

In an embodiment, the dental appliance has lingual tabs adjacent to the occlusal surface wherein the lingual tabs extend rearward into the mouth when the base is placed within the mouth.

In an embodiment, the dental appliance has a shield extending from the occlusal surface wherein the shield covers the teeth when the base is placed within the mouth.

In an embodiment, the dental appliance has a wall extending from the occlusal surface wherein the wall exerts a force against teeth when the base is placed within the mouth.

In another embodiment of the present invention, a system of dental appliances is provided wherein each of the dental appliances has a length defined between a first end and a second end and wherein each of the dental appliances is placed within the mouth of a user having upper teeth and lower teeth. The system has a first dental appliance having a generally U-shaped upper base which contacts upper teeth of the user when the upper base is placed within the mouth. The system also has a second dental appliance having a generally U-shaped lower base wherein the lower base contacts lower teeth of the user when the lower base is placed within the mouth and wherein the upper base is adjacent to the lower base and wherein the upper base and the lower base define an interior surface having a concave portion. In addition, the system has a reline material in contact with the concave portion wherein the reline material prevents the upper base and the lower base from sliding when placed within the mouth.

In an embodiment, the system has a shield extending from the upper base wherein the shield covers the teeth when the upper base is placed in the mouth.

In an embodiment, the first dental appliance is thicker at the second end than at the first end wherein the first end is adjacent to an exterior of the mouth when the first dental appliance and the second dental appliance are placed within the mouth.

In an embodiment, the second dental appliance is thicker at the second end than at the first end wherein the first end is adjacent to an exterior of the mouth when the second dental appliance and the first dental appliance are placed within the mouth.

In an embodiment, the system has a shield extending from the concave portion wherein the shield covers the teeth when the first dental appliance and the second dental appliance are placed within the mouth.

In an embodiment, the system has an occlusal surface on the first dental appliance wherein the occlusal surface contacts the upper teeth when the first dental appliance is placed within the mouth wherein the occlusal surface is flat.

In an embodiment, the system has a hinge connecting the first dental appliance and the second dental appliance.

In an embodiment, the system has a socket formed within the first dental appliance wherein the socket is shaped to receive at least one of the teeth of the user.

In an embodiment, the first dental appliance is constructed from a first material and a second material wherein the first material has a lesser degree of rigidity than the second material.

In an embodiment, the first dental appliance and the second dental appliance are sized to contact at least one but not all of the teeth when the first dental appliance and the second dental appliance are placed within the mouth.

In an embodiment, the reline material adheres to the upper teeth.

In an embodiment, the system has a substance between the reline material and the concave portion wherein the substance enables the reline material to adhere to the concave portion.

In an embodiment, the system has wedges formed within the first dental appliance and the second dental appliance wherein the wedges force the lower teeth to be held forward in relation to the upper teeth.

In an embodiment, the system has lingual tabs formed within the second dental appliance wherein the lingual tabs extend rearward into the mouth when the second dental appliance is placed within the mouth.

In another embodiment of the present invention, a dental appliance is provided which has a length defined between a first and a second end wherein the dental appliance is placed within a mouth of a user having upper teeth and lower teeth. The dental appliance has a generally U-shaped upper base having an upper occlusal surface wherein the upper occlusal surface contacts the upper teeth. The dental appliance also has a generally U-shaped lower base connected to the upper base wherein the lower base has a lower occlusal surface wherein the lower occlusal surface contacts the lower teeth. In addition, the dental appliance has a hinge insertable within the upper base and the lower base wherein the hinge connects the upper base and the lower base. Further, the dental appliance has a reline material in contact with the upper occlusal surface wherein the reline material prevents the upper base from sliding when placed within the mouth.

In an embodiment, the upper base is thicker at the first end than at the second end wherein the first end is adjacent to an exterior of the mouth when the upper base and the lower base are placed within the mouth.

In an embodiment, the dental appliance has a solvent positioned between the reline material and the occlusal surface wherein the solvent enables the reline material to adhere to the occlusal surface.

In an embodiment, the upper base is thicker at the second end than at the first end wherein the first end is adjacent to an exterior of the mouth when the upper base and the lower base are placed within the mouth.

In an embodiment, the occlusal surface is flat.

In an embodiment, the upper base is roughened.

In an embodiment, the dental appliance has a mark on the upper base indicating an amount of reline material in contact with the upper base.

In an embodiment, the dental appliance has a socket formed within the upper base wherein the socket is shaped to receive at least one of the teeth of the user.

In an embodiment, the upper base is sized to contact at least one but not all of the teeth when the upper base is placed within the mouth.

In an embodiment, the reline material adheres to the upper teeth.

In an embodiment, the dental appliance has the lower base increases in rigidity from the first end to the second end.

In an embodiment, the dental appliance has lingual tabs adjacent to the lower base wherein the lingual tabs extend rearward into the mouth when the lower base is placed within the mouth.

In an embodiment, the upper base is constructed from a first material and a second material wherein the first material has a lesser degree of rigidity than the second material.

In another embodiment of the present invention, a dental appliance is provided which has a length defined between a first and a second end wherein the dental appliance is placed in a mouth of a user having upper teeth and lower teeth. The dental appliance has a generally U-shaped upper base having an upper occlusal surface wherein the upper occlusal surface contacts the upper teeth. The dental appliance also has a generally U-shaped lower base connected to the upper base wherein the lower base has a lower occlusal surface wherein the lower occlusal surface contacts the lower teeth. The dental appliance also has a hinge integrally formed with the upper base and the lower base wherein the hinge connects the upper base and the lower base. Further, the dental appliance has a reline material in contact with the upper occlusal surface wherein the reline material prevents the upper base from sliding when placed within the mouth.

In an embodiment, the reline material surrounds the occlusal surface.

In an embodiment, the upper base is thicker at the first end than at the second end wherein the first end is adjacent to an exterior of the mouth when the upper base and the lower base are placed within the mouth.

In an embodiment, the dental appliance has a solvent positioned between the reline material and the occlusal surface wherein the solvent enables the reline material to adhere to the occlusal surface.

In an embodiment, the upper base is thicker at the second end than at the first end wherein the first end is adjacent to an exterior of the mouth when the upper base and the lower base are placed within the mouth.

In an embodiment, the occlusal surface is flat.

In an embodiment, the upper base is roughened.

In an embodiment, the dental appliance has a mark on the upper base indicating an amount of reline material in contact with the upper base.

In an embodiment, the dental appliance has a socket formed within the upper base wherein the socket is shaped to receive at least one of the teeth of the user.

In an embodiment, the upper base is sized to contact at least one but not all of the teeth when the upper base is placed within the mouth.

In an embodiment, the reline material adheres to the upper teeth.

In an embodiment, the lower base increases in rigidity from the first end to the second end.

In an embodiment, the dental appliance has lingual tabs adjacent to the lower base wherein the lingual tabs extend rearward into the mouth when the lower base is placed within the mouth.

In an embodiment, the upper base is constructed from a first material and a second material wherein the first material has a lesser degree of rigidity than the second material.

In another embodiment of the present invention, a method is provided for treating a malocclusion of a user having a mouth having one or more teeth. The method comprises the steps of: diagnosing the user with the malocclusion; determining an amount of time the user is required to place the dental appliance within the mouth on a periodic basis wherein the dental appliance has a generally U-shaped base and further has a socket within the base sized to receive at least one or more teeth of the user and wherein the dental appliance corrects the malocclusion; and wearing the dental appliance for less than the amount of time required while extending the periodic basis.

In an embodiment, the method has the further step of depositing a reline material onto the dental appliance to prevent the dental appliance from slipping within the mouth when the dental appliance is placed within the mouth In an embodiment, the method has the further step of biting the dental appliance when the dental appliance is placed within the mouth.

It is, therefore, an advantage of the present invention to provide a dental appliance, a system and a method for reducing an amount of patient cooperation required for treating a malocclusion using the dental appliance.

Another advantage of the present invention is to provide a dental appliance, a system and a method for reducing an amount of patient cooperation required for treating a malocclusion using the dental appliance which may reduce an amount of time required for treating the malocclusion.

Yet another advantage of the present invention is to provide a dental appliance, a system and a method for reducing an amount of patient cooperation required for treating a malocclusion using the dental appliance which may reduce an amount of exercise required by the patient to treat the malocclusion.

Another advantage of the present invention is to provide a dental appliance, a system and a method for reducing an amount of patient cooperation required for treating a malocclusion using the dental appliance wherein a patient may wear the dental appliance during a period of nighttime passive wear.

And, an advantage of the present invention is to provide a dental appliance, a system and a method for reducing an amount of patient cooperation required for treating a malocclusion wherein a greater percentage of patients may be motivated to wear the dental appliance to treat the malocclusion.

Still another advantage of the present invention is to provide a dental appliance, a system and a method for reducing an amount of patient cooperation required for treating a malocclusion which may adhere to the teeth of the patient to correct, for example, rotations, crowding and/or spacing with passive wear of the dental appliance during, for example, sleeping.

Yet another advantage of the present invention is to provide a dental appliance, a system and a method for reducing an amount of patient cooperation required for treating a malocclusion wherein the dental appliance is shortened posteriorly to eliminate any material occlusally contacting the teeth, which may encourage posterior permanent molars to erupt, thereby correcting excessive overbite during passive nighttime wear by the patient.

Moreover, an advantage of the present invention is to provide a dental appliance, a system and a method for reducing an amount of patient cooperation required for treating a malocclusion which utilizes a sticky substance in an arch of the dental appliance requiring a greatest amount of tooth movement, or upon the teeth of the user, which may enable the dental appliance to be retained and straighten rotations during passive nighttime wear.

Another advantage of the present invention is to provide a dental appliance, a system and a method for reducing an amount of patient cooperation required for treating a malocclusion wherein the dental appliance may be fabricated out of a sticky plastic or a solvent or a sticky substance is sprayed on an inside surface of the appliance to increase an adherence of the dental appliance to the teeth.

A further advantage of the present invention is to provide a dental appliance, a system and a method for reducing an amount of patient cooperation required for treating a malocclusion using the dental appliance wherein the dental appliance causes the lower jaw to advance anteriorly relative to the upper jaw to correct overjet during passive nighttime wear and to allow for posterior eruption.

Another advantage of the present invention is to provide a dental appliance, a system and a method for reducing an amount of patient cooperation required for treating a malocclusion which may have a hinge which may forcibly open the dental appliance in the mouth while the patient sleeps and may accelerate the correction of malocclusions, such as, for example, overbite, overjet, rotations, crowding and spacing by retaining a position of the dental appliance within the mouth.

Moreover, an advantage of the present invention is to provide a dental appliance, a system and a method for reducing an amount of patient cooperation required for treating a malocclusion wherein a single-arched dental appliance having a reline material may be worn passively at night and/or during the day to correct crowding, rotations and spacing wherein a user may bite down on the dental appliance.

Yet another advantage of the present invention is to provide a dental appliance, a system and a method for reducing an amount of patient cooperation required for treating a malocclusion wherein a single-arched dental appliance which may have a reline material may be worn as a retainer following correction of crowding, rotations and/or spacing.

Still another advantage of the present invention is to provide a dental appliance, a system and a method for reducing an amount of patient cooperation required for treating a malocclusion wherein a single-arched dental appliance which may have a reline material may be retained within the mouth while, for example, sleeping or otherwise resting.

A further advantage of the present invention is to provide a dental appliance, a system and a method for reducing an amount of patient cooperation required for treating a malocclusion wherein a single-arched dental appliance which may have a reline material may place pressure on the front and/or rear teeth.

Another advantage of the present invention is to provide a dental appliance, a system and a method for reducing an amount of patient cooperation required for treating a malocclusion wherein a single-arched dental appliance which may have a reline material may encourage eruption of posterior teeth.

And, another advantage of the present invention is to provide a dental appliance, a system and a method for reducing an amount of patient cooperation required for treating a malocclusion wherein a single-arched dental appliance which may have a reline material may be worn solely in an upper arch or in a lower arch.

Moreover, an advantage of the present invention is to provide a dental appliance, a system and a method for reducing an amount of patient cooperation required for treating a malocclusion wherein two single-arched dental appliances which may have a reline material may be worn on a lower arch and an upper arch simultaneously.

Yet another advantage of the present invention is to provide a dental appliance, a system and a method for reducing an amount of patient cooperation required for treating a malocclusion wherein a single-arched dental appliance which may have a reline material may be sized to enable the last molar to super-erupt and reduce an overbite.

A further advantage of the present invention is to provide a dental appliance, a system and a method for reducing an amount of patient cooperation required for treating a malocclusion wherein a double-arched dental appliance which may have a reline material may maintain teeth which have been corrected from conditions such as, for example, crowding, rotations and spacing without requiring a biting force to be applied by a user.

Another advantage of the present invention is to provide a dental appliance, a system and a method for reducing an amount of patient cooperation required for treating a malocclusion wherein a double-arched dental appliance which may have a reline material may correct crowding, rotations and spacing vis-a-vis passive wear by a user.

Still another advantage of the present invention is to provide a dental appliance, a system and a method for reducing an amount of patient cooperation required for treating a malocclusion wherein the dental appliance has one or more shields which are longer and thicker than known dental appliances which may prevent movement of the dental appliance away from teeth and may provide movement of teeth into a correct position.

Moreover, an advantage of the present invention is to provide a dental appliance, a system and a method for reducing an amount of patient cooperation required for treating a malocclusion wherein the dental appliance may have a rib formed in an area which contacts front teeth to provide pressure against front teeth.

Yet another advantage of the present invention is to provide a dental appliance, a system and a method for reducing an amount of patient cooperation required for treating a malocclusion wherein a front end of the dental appliance may be bent gingivally to provide overbite correction.

Still further, an advantage of the present invention is to provide a dental appliance, a system and a method for reducing an amount of patient cooperation required for treating a malocclusion wherein a double-arched dental appliance having a reline material may encourage teeth to erupt through passive wear.

Moreover, an advantage of the present invention is to provide a dental appliance, a system and a method for reducing an amount of patient cooperation required for treating a malocclusion wherein shields extending from the dental appliance are higher and thicker than known dental appliances and wherein the dental appliance has a retentive ability which may prevent the dental appliance from slipping from the teeth and may move the teeth efficiently.

Yet another advantage of the present invention is to provide a dental appliance, a system and a method for reducing an amount of patient cooperation required for treating a malocclusion wherein two single-arched dental appliances which may have a reline material may be worn on both lower teeth and upper teeth simultaneously.

And, an advantage of the present invention is to provide a dental appliance, a system and a method for reducing an amount of patient cooperation required for treating a malocclusion wherein two single-arched dental appliances may have wedges incorporated into posterior sections, on both sides of the dental appliances, to force the lower-worn dental appliance to be positioned in a forward position in relation to the upper-worn dental appliance, which may correct Class II (mandibular retrusions) relations.

Another advantage of the present invention is to provide a dental appliance, a system and a method for reducing an amount of patient cooperation required for treating a malocclusion wherein the dental appliance may have an interior surface which may have a multiple socket or slot for more than one tooth.

A further advantage of the present invention is to provide a dental appliance, a system and a method for reducing an amount of patient cooperation required for treating a malocclusion wherein two dental appliances which may contact upper teeth and lower teeth may each have a shield that extends upward and downward beyond the gingival margins in a front section of the dental appliances on both a labial side and a lingual side.

Yet another advantage of the present invention is to provide a dental appliance, a system and a method for reducing an amount of patient cooperation required for treating a malocclusion wherein reline material may be placed into gingival embrasures (interproximally), labially and lingually on a first dental appliance which contacts upper teeth and a second dental appliance which contacts lower teeth, without reline material placed adjacent crowns of the front teeth, to enable a front of the dental appliances to be forced against front teeth while straightening the crowns.

Another advantage of the present invention is to provide a dental appliance, a system and a method for reducing an amount of patient cooperation required for treating a malocclusion wherein a ridge of material or buttons of material are formed along the dental appliance at a mesial margin and a distal margin of the dental appliance to rotate the teeth.

Moreover, advantage of the present invention is to provide a dental appliance, a system and a method for reducing an amount of patient cooperation required for treating a malocclusion wherein a front segment of an upper dental appliance and a lower dental appliance, mesial to the canine area, may be shaped towards a gingival section of the upper front teeth and/or lower front teeth to provide a depressive force against front teeth and to rotate teeth.

A still further advantage of the present invention is to provide a dental appliance, a system and a method for reducing an amount of patient cooperation required for treating a malocclusion wherein two single-arched dental appliances may be worn simultaneously to advance a mandible to a super Class I relation, or slightly short of an end-to-end relation of a front section of the mouth.

And, another advantage of the present invention is to provide a dental appliance, a system and a method for reducing an amount of patient cooperation required for treating a malocclusion wherein the dental appliance may cause a lower jaw to advance forward in relation to the upper jaw into a Class III relation.

Additional features and advantages of the present invention are described in, and will be apparent from, the detailed description of the presently preferred embodiments and from the drawings.

BRIEF DESCRIPTION OF THE DRAWINGS

FIG. 10 illustrates a perspective view of a dental appliance in an embodiment of the present invention.

FIG. 11 illustrates a perspective view of a dental appliance in an embodiment of the present invention.

DETAILED DESCRIPTION OF THE PRESENTLY PREFERRED EMBODIMENTS

The present invention relates to a dental appliance, a system and a method for treating a malocclusion using the dental appliance wherein a patient may require a lesser amount of cooperation to treat the malocclusion. More specifically, the present invention relates to a dental appliance which may cause teeth of the user to move into a corrected position. Moreover, the patient may not be required to perform an amount of exercise, or like cooperational action, normally required by the patient to correct and/or to assist with the correction of the malocclusion. In other embodiments, the method of exercise or cooperation may reduce an amount of time the dental appliance is worn in the mouth of the patient.

Figure 1:
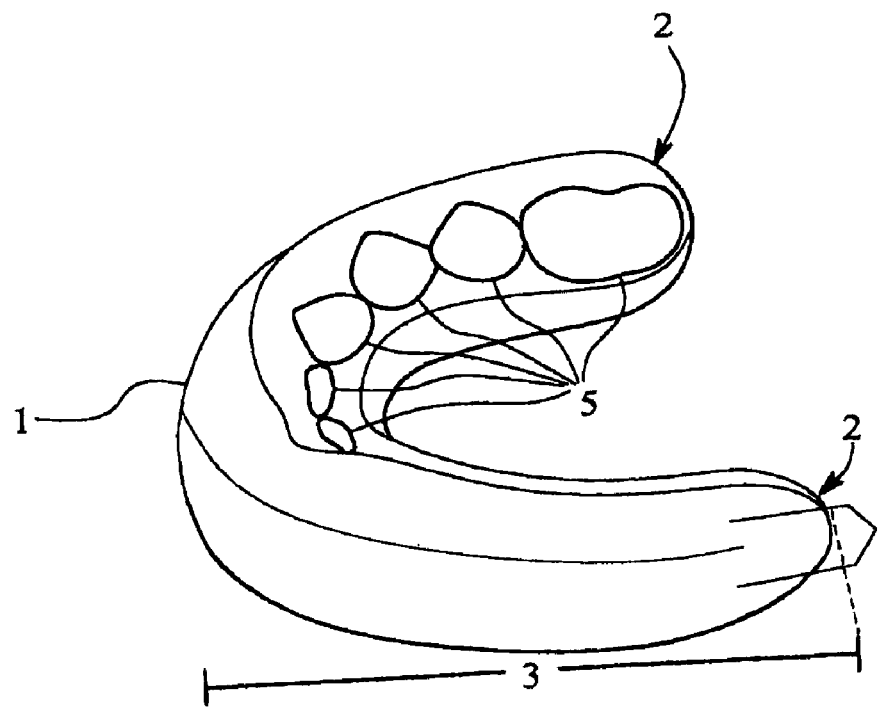
FIG. 1 illustrates a perspective view of a dental appliance in an embodiment of the present invention.

Referring now to the drawings, wherein like numerals refer to like parts, FIG. 1 illustrates a dental appliance 1 which may be worn by a patient of approximately twelve years of age or older having a permanent dentition. The dental appliance 1 may be constructed from rubber, plastic or like material. The dental appliance 1 may have sockets 5 for receiving teeth of the patient.

Figure 2:
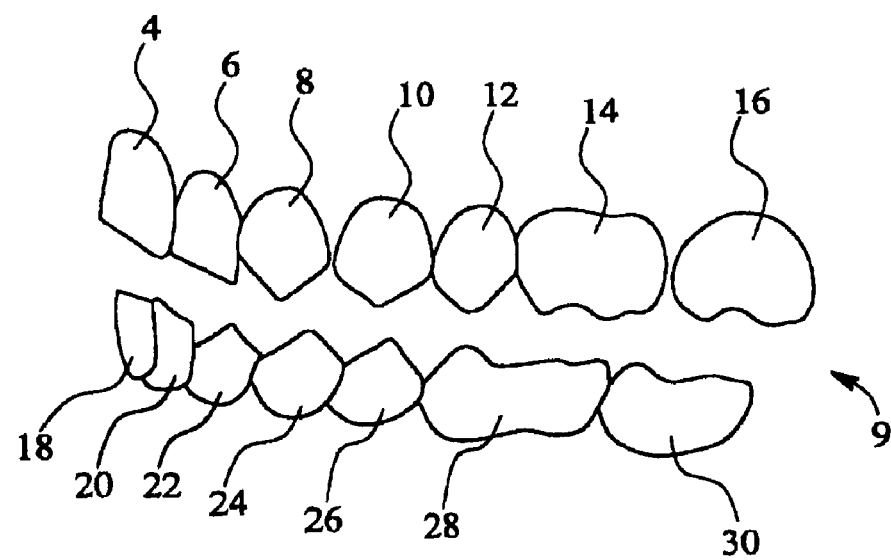
FIG. 2 illustrates a side view of teeth of a patient.

In an embodiment, the dental appliance 1 may have a length 3 wherein the dental appliance 1 during its wear may extend rearward to the first permanent molars 14, 28 illustrated in a profile 9 of teeth 4, 6, 8, 10, 12, 14, 16, 18, 20, 22, 24, 26, 28 and 30 in FIG. 2. Posterior ends 2 may be positioned toward a rear of the mouth of the patient when the dental appliance 1 is worn by the patient. Because of the shortened length 3 of the dental appliance 1, the posterior ends 2 may not cover second permanent molars 16, 30 of the patient. The second permanent molars 16, 30 may then erupt beyond a normal vertical position in an occlusion of the patient. Movement of the teeth may reduce an amount of exercise or cooperation required for treatment of the malocclusion, particularly an overbite.

Figure 3:
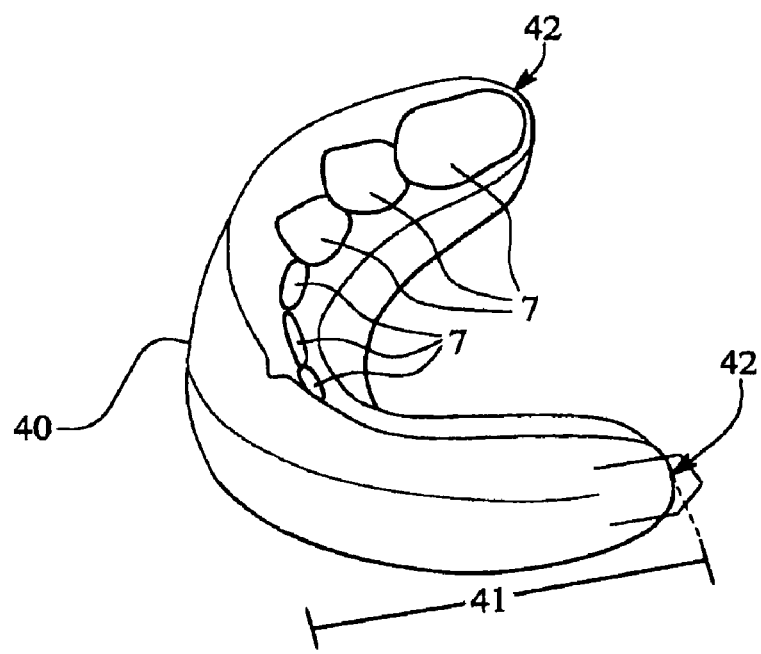
FIG. 3 illustrates a perspective view of a dental appliance in an embodiment of the present invention.
Figure 4:
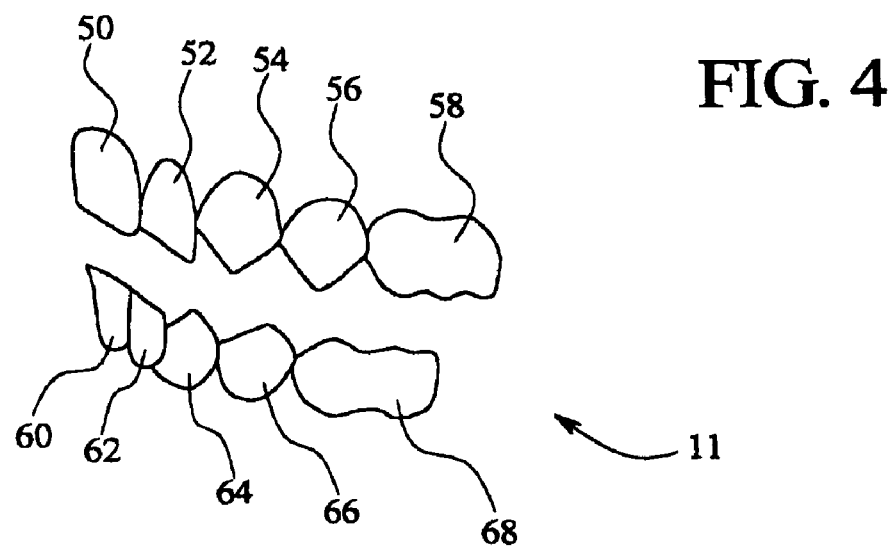
FIG. 4 illustrates a side view of teeth of a patient.

FIG. 3 illustrates a dental appliance 40 which may be worn by a patient of approximately seven to twelve years of age having a mixed dentition. The dental appliance 40 may be constructed from rubber, plastic or like material. The dental appliance 40 may have sockets 7 for receiving the teeth of the patient. The dental appliance 40 may have a length 41 wherein posterior ends 42 of the dental appliance 40, when worn, may extend to second deciduous molars 58, 68, as illustrated in a profile 11 of teeth 50, 52, 54, 56, 58, 60, 62, 64, 66 and 68 in FIG. 4. As a result, the first permanent molars 14, 28, and/or the second permanent molars 16, 30, illustrated in FIG. 2, may super-erupt. The first permanent molars 14, 28 and/or the second permanent molars 16, 30 may then drive the jaws of the patient open and reduce an overbite of the patient. Accordingly, the dental appliance 40 may be worn by the patient at night while the patient is, for example, sleeping. Preferably, the patient may treat the malocclusion through nighttime wear only. Further, movement of the teeth may reduce an amount of exercise or other cooperation required for treatment of a malocclusion.

In an embodiment, the dental appliances 1, 40 may be constructed, either entirely or partially, from a plastic having an adhesive layer (not shown). As a result, the adhesive layer may cause the dental appliances 1, 40 to adhere to the teeth of the patient when the teeth are, for example, dry and/or free of moisture. In an embodiment, the sockets 5, 7 of the dental appliances 1, 40 respectively, may be constructed from a soft plastic.

Figure 5:
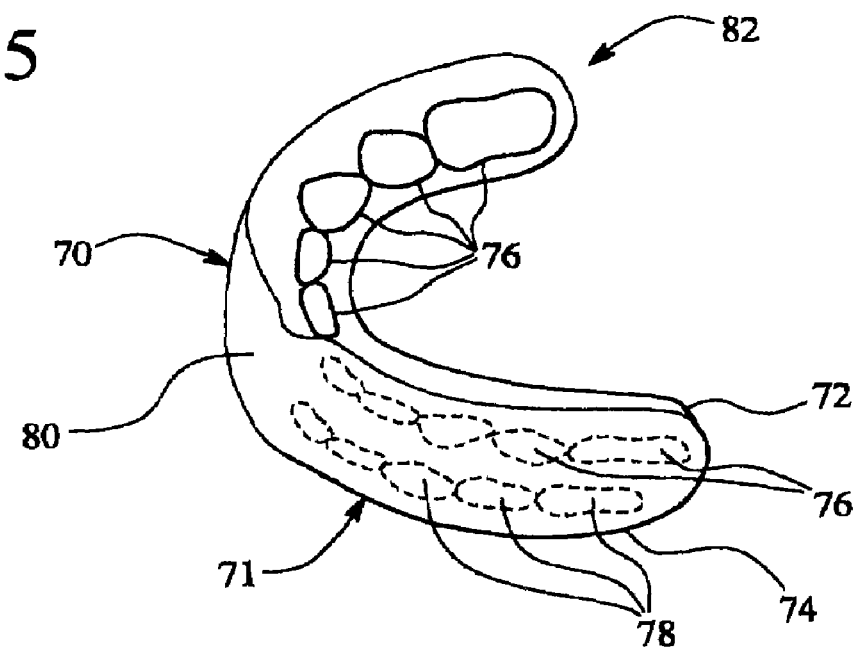
FIG. 5 illustrates a perspective view of a dental appliance in an embodiment of the present invention.

FIG. 5 illustrates a dental appliance 70 which may have upper sockets 76 and lower sockets 78 constructed from, for example, a soft plastic. A base 71 of the dental appliance 70 and margins 72, 74 may be constructed from, for example, a stiffer plastic. In another embodiment, a front portion 80 of the dental appliance 70 may be constructed from a soft, adhering material; a rear portion 82 of the dental appliance 82 may be constructed from a stiffer material, such as, for example, a hard plastic or rubber.

Figure 6A:
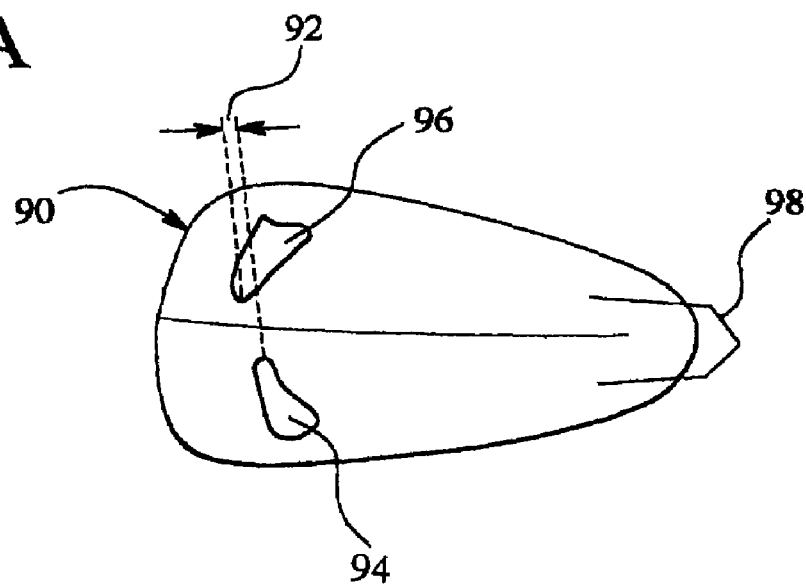
FIG. 6A illustrates a side view of a dental appliance in an embodiment of the present invention.
Figure 6B:
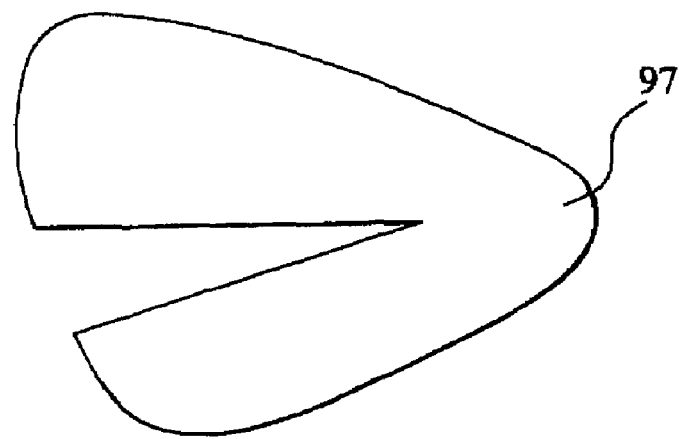
FIG. 6B illustrates a side view of a dental appliance in an embodiment of the present invention.

FIG. 6A illustrates a dental appliance 90 which may have a socket 94 for receiving a lower incisor and a socket 96 for receiving an upper incisor. The dental appliance 90 may create a jaw relation that advances the lower jaw of the patient and provides a minimal or non-existent overjet distance 92. The dental appliance 90 may also have a hinging mechanism 98 which may be provided separately. In an embodiment illustrated in FIG. 6B, a dental appliance 97 may be shaped or molded to have a hinging action. The hinging mechanism 98 or hinging action may allow the dental appliances 90, 97 to open and close with the upper jaw and the lower jaw of the patient. The combination of the minimal overjet distance 92 and the hinging mechanism 98 or hinging action may assist the lower jaw to advance towards a front of the mouth of the patient while the patient is sleeping to better correct an overjet.

Figure 7:
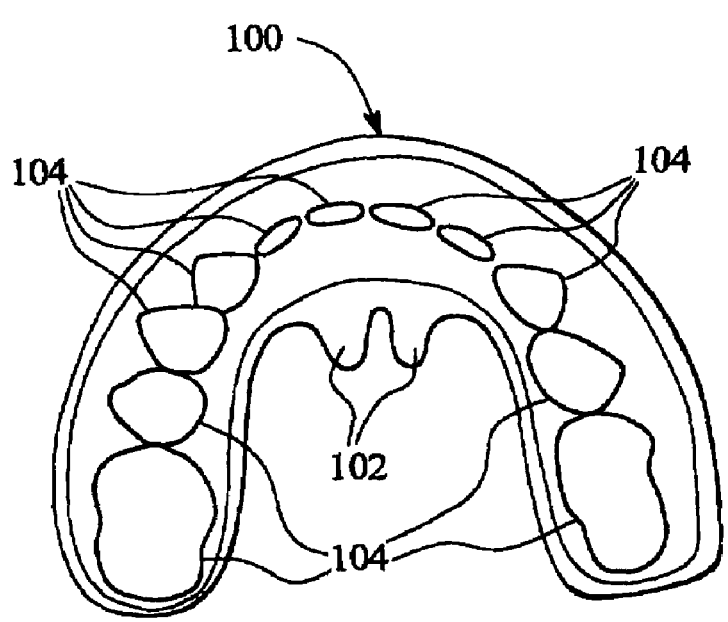
FIG. 7 illustrates a top plan view of a dental appliance in an embodiment of the present invention.

In an embodiment, as illustrated in FIG. 7, a dental appliance 100 is provided having sockets 104. The dental appliance 100 may have extended lingual tabs 102 to assist the lower jaw of the patient to be held towards the front of the mouth of the patient.

Further, any of the dental appliances 1, 40, 70, 90, 97 and/or 100 may have an adhesive material or other like adhesive inserted into the sockets 5, 7, 76, 78, 94, 96 and 104 of the dental appliances 1, 40, 70, 90, 97 and/or 100 respectively. The adhesive material may allow the dental appliances 1, 40, 70, 90, 97 and/or 100 to adhere to the teeth and prevent the dental appliances 1, 40, 70, 90, 97 and/or 100 from slipping from the mouth of the patient.

In an embodiment, the patient may perform exercises which may correct malocclusions while requiring a lesser amount of cooperation than required with known dental appliances. For example, the patient may bite and/or clench into a dental appliance for a time period of five to ten minutes while clenching and/or biting during the time period. As a result, the patient may reduce a need for wearing the dental appliance during, for example, the daytime. The exercises may also be performed in conjunction with wearing any of the dental appliances 1, 40, 70, 90, 97 and/or 100.

In another embodiment, the patient may reduce an amount of time a dental appliance is worn when the patient is awake or active. However, an overall time period during which a malocclusion is treated may be extended. In an example, the overall time period for the patient to treat the malocclusion may be extended from a period of four to ten months, to two years with reduced wearing of the dental appliance during the time the patient is awake or active. The reduction of time the dental appliance is worn by the patient may be performed in conjunction with known dental appliances, or with any of the dental appliances 1, 40, 70, 90, 97 and/or 100.

Figure 8:
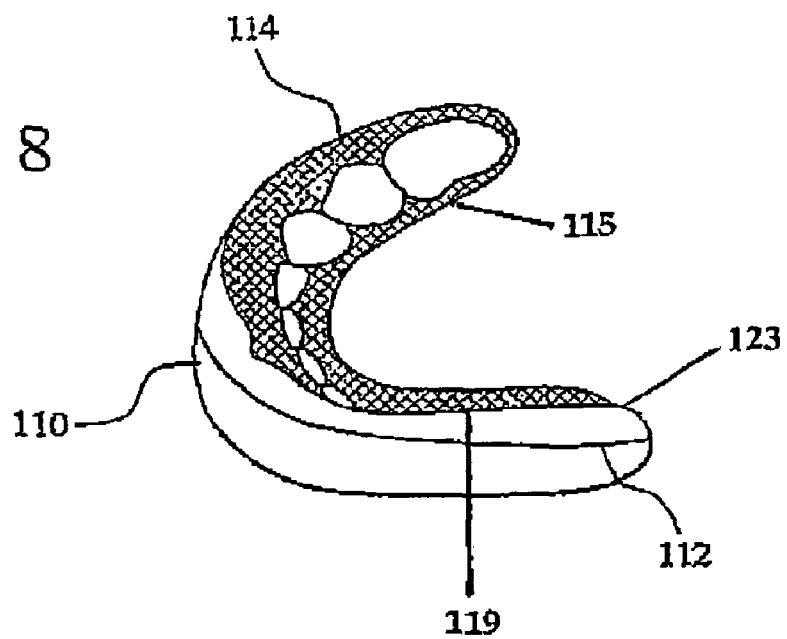
FIG. 8 illustrates a perspective view of an upper shell of a dental appliance in an embodiment of the present invention.
Figure 9:
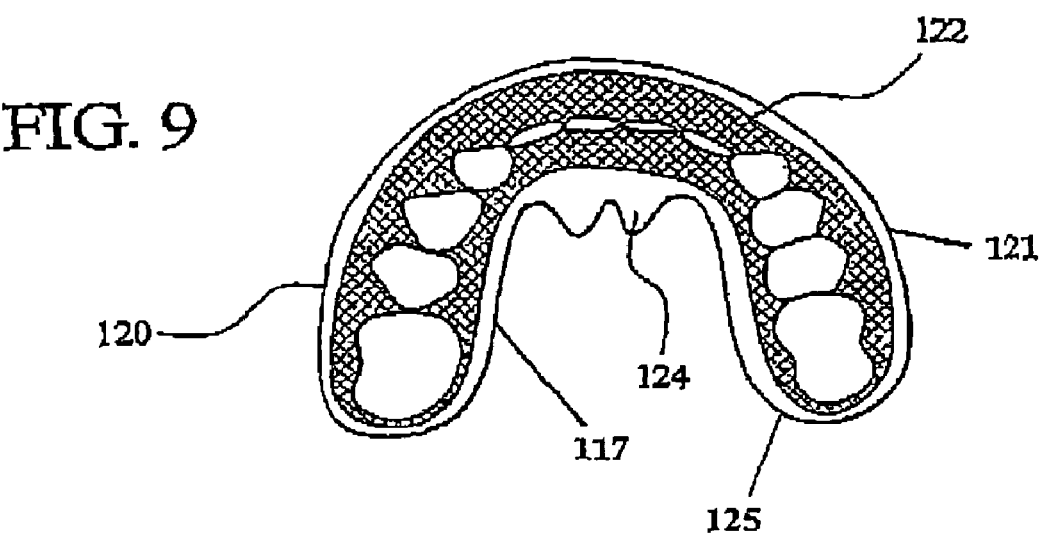
FIG. 9 illustrates a perspective view of a lower shell of a dental appliance in an embodiment of the present invention.

In an embodiment, a method is provided which may increase retention of any of the dental appliances 1, 40, 70, 90, 97 and/or 100. FIGS. 8 and 9 illustrate an upper shell 110 and/or a lower shell 120 which may be combined to create a dental appliance 130. The lower shell may have lingual tabs 124. The upper shell 110 and the lower shell 120 may receive a reline material 132, as illustrated in FIG. 10. The upper shell 110 and/or the lower shell 120 may have roughened, or coarse surfaces 114, 122, respectively, along lingual shields 115, 117 and/or buccal shields 119, 121 to secure the reline material 132. The roughened surfaces 114, 122 may prevent the reline material 132 from becoming disengaged from the upper shell 110 and/or the lower shell 120. The lingual shields 115, 117 and the buccal shields 119, 121 may have a mark 112 placed on the roughened surfaces 114, 122. The mark 112 may serve as a guide when placing the reline material 132 onto the upper shell 110 and/or the lower shell 120. In an embodiment, the reline material 132 may be injected from, for example, a syringe 134.

It is generally known that crowding, rotation and spacing problems are present in the front teeth. Accordingly, the upper shell 110 and/or the lower shell 120 may be worn to treat these malocclusions. The reline material 132 may be utilized in areas of the upper shell 110 and/or the lower shell 120 which do not require tooth movement. As a result, the reline material 132 may provide retention sufficient to prevent the upper shell 110 and/or the lower shell 120 from being dislodged during wear.

The reline material 132 may be injected or inserted into areas of the upper shell 110 and/or the lower shell 120 which may not require tooth movement. The mark 112 may indicate an appropriate amount of reline material 132 to be deposited. Accordingly, the mark 112 may reduce a need for removal of excess reline material 132 from the upper shell 110 and/or the lower shell 120. The dental appliance 130 may be inserted within the mouth while securing teeth requiring movement within respective sockets.

In an embodiment, after applying the reline material 132, the user may press the upper shell 110 and/or the lower shell 120 forcibly against the front teeth. A rear portion 123, 125 of the upper shell 110 and/or the lower shell 120 may then be forcibly pushed down on the teeth. The user may then bite down to maintain the upper shell 110 and/or the lower shell 120 under pressure until the reline material 132 has completely set. A cotton roll (not shown) positioned on the occlusal surface of the teeth of the user may assist in maintaining a proper amount of pressure. When the reline material is completely set, the upper shell 110 and/or the lower shell 120 may be removed from the mouth. In an embodiment, the user may be instructed to wear the upper shell 110 and/or the lower shell 120 while, for example, sleeping, or otherwise resting. To expedite movement of the teeth, the upper shell 110 and/or the lower shell 120 may also be worn during the daytime. If space is required within the mouth of the user due to crowding of teeth, one or more teeth may be stripped prior to wearing of the upper shell 110 and/or the lower shell 120.

A second dental appliance 140, illustrated in FIG. 11, may be worn after crooked or spaced teeth are straightened. The dental appliance may have an upper shell 146 and a lower shell 144 which are connected. The dental appliance 140 may receive reline material 132 (not shown in FIG. 11) which may be placed on the dental appliance 140 in any areas in which teeth are contacted. The dental appliance 140 may have a hinge 142 which may allow opening of the jaws to provide comfort to the user. The dental appliance 140 may assist in correcting overjet and/or overbite. If overjet and/or overbite are not present, the dental appliance 140 may not be required by the user. In such a case, the upper shell 110 and/or the lower shell 120 may be used as a retainer. The reline material 132 may be placed along newly straightened teeth prior to wear of the dental appliance 140.

If the dental appliance 140 is required to correct existing overjet and/or overbite or to guide erupting teeth, the reline material 132 may be placed along the upper teeth and the lower teeth (not shown) of the user. The reline material 132 may secure the dental appliance 140 to serve as a retainer. The dental appliance 140 may be worn only at night, or when the user is at rest or asleep. However, in cases of severe overjet and/or overbite, or if treatment is to be expedited, the dental appliance 140 may be worn when the user is, for example, awake or active. In such a case, one or more hours of exercise, including biting into the dental appliance 140, may be required by the user.

Figure 12:
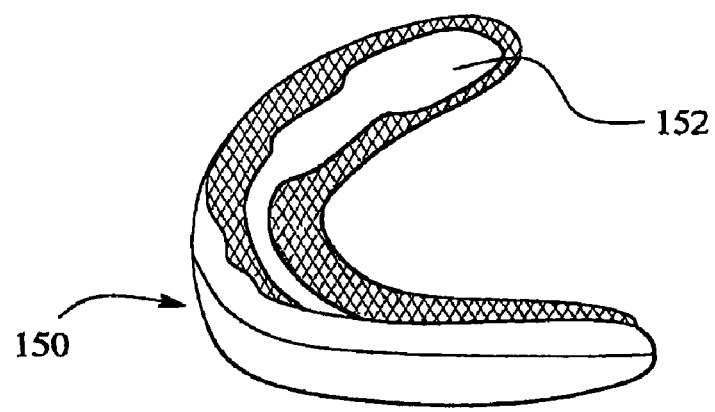
FIG. 12 illustrates a perspective view of a dental appliance in an embodiment of the present invention.
Figure 13:
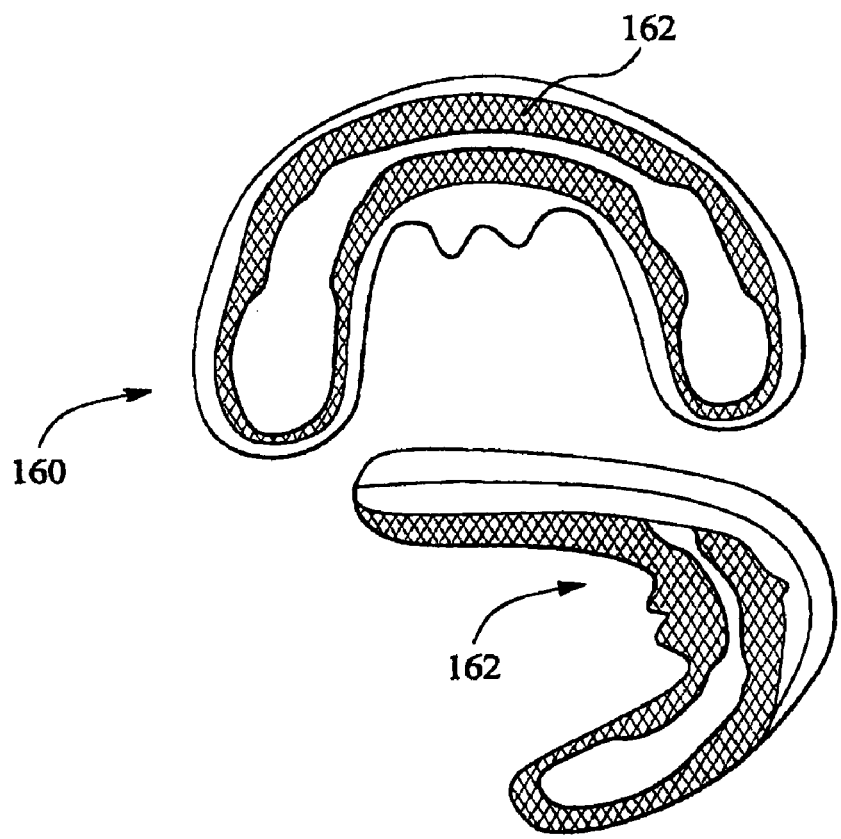
FIG. 13 illustrates a perspective view of a dental appliance in an embodiment of the present invention.

In an embodiment, illustrated in FIGS. 12 and 13, two or more dental appliances may be worn to treat a malocclusion. A first dental appliance may be a one-size-fits-all type dental appliance 150,160. The first dental appliance 150, 160 may be socketless. In another embodiment, the first dental appliance may be a socketed dental appliance 130. In another embodiment, the first dental appliance may be a partially socketed dental appliance (not shown) which may be preformed or custom made. A second dental appliance may be a socketed or partially socketed dental appliance (not shown) which may be either preformed or custom made. In an embodiment, the second dental appliance may be a completely socketless, one-size-fits-all type dental appliance 150,160.

It should be understood that various changes and modifications to the presently preferred embodiments described herein will be apparent to those skilled in the art. Such changes and modifications may be made without departing from the spirit and scope of the present invention and without diminishing its attendant advantages.

I claim:

1. A dental appliance which is placed in a mouth of a user wherein the user has upper teeth and lower teeth, the dental appliance comprising:
    a generally U-shaped base having a length defined between a first end and a second end wherein the base has an upper occlusal surface and a lower occlusal surface which are sized to receive the upper teeth or the lower teeth of the user wherein the upper occlusal surface contacts the upper teeth of the user when the base is placed within the mouth wherein the lower occlusal surface contacts the lower teeth of the user when the base is placed within the mouth of the user wherein the base has an interior surface which substantially surrounds a surface of at least one of the upper teeth and at least one of the lower teeth wherein the first end has a rear portion which is made from a first material and the second end has a front portion which is made from a second material wherein the first material is stiffer than the second material wherein the second material moves at least one of the upper teeth of the user or at least one of the lower teeth of the user when the base is worn in the mouth of the user.

2. The dental appliance of claim 1 wherein the interior surface is roughened.

3. The dental appliance of claim 1 wherein the occlusal surface is flat.

4. The dental appliance of claim 1 further comprising:
    a mark on the interior surface indicating an amount of reline material in contact with the interior surface wherein the interior surface prevents the reline material from disengaging from the generally U-shaped base.

5. The dental appliance of claim 1 further comprising:
    a socket formed within the interior surface wherein the socket is shaped to receive a tooth of the user.

6. The dental appliance of claim 1 wherein the upper occlusal surface is movable with respect to the lower occlusal surface wherein the front end of the upper occlusal surface is separable from the front end of the lower occlusal surface.

7. The dental appliance of claim 1 wherein the base is sized to contact at least one tooth but not all teeth when the base is placed within the mouth.

8. The dental appliance of claim 1 wherein the interior surface adheres to at least one of the teeth.

9. The dental appliance of claim 1 wherein the base increases in rigidity from the front portion to the rear portion.

10. The dental appliance of claim 1 further comprising:
    lingual tabs adjacent to the occlusal surface wherein the lingual tabs extend rearward into the mouth when the base is placed within the mouth.

11. The dental appliance of claim 1 further comprising:
    a shield extending from the occlusal surface wherein the shield covers the teeth when the base is placed within the mouth.

12. The dental appliance of claim 1 further comprising:
    a wall extending from the occlusal surface wherein the wall exerts a force against teeth when the base is placed within the mouth.

13. A system of dental appliances wherein each of the dental appliances has a length defined between a first end and a second end and wherein each of the dental appliances is placed within the mouth of a user having upper teeth and lower teeth wherein the mouth of the user has an incisor and a molar, the system comprising;
    a first dental appliance having a generally U-shaped upper base which contacts upper teeth of the user when the upper base is placed within the mouth;
    a second dental appliance having a generally U-shaped lower base wherein the lower base contacts lower teeth of the user when the lower base is placed within the mouth and wherein the upper base is adjacent to the lower base and wherein the upper base and the lower base define an interior surface having a concave portion wherein the first dental appliance and the second dental appliance are made from a first material and a second material wherein the first material is stiffer than the second material wherein a front portion of the upper base and the lower base is adjacent to the second material and the incisor in the mouth of the user and further wherein a rear portion of the upper base and the lower base is adjacent to the first material and the molar in the mouth of the user; and
    a hinge connecting the second material of the upper base to the second material of the lower base wherein the concave portion and the hinge prevent the upper base and the lower base from sliding when placed within the mouth wherein the hinge is made from a third material wherein the third material is stiffer than the first material.

14. The system of claim 13 further comprising:
    a shield extending from the upper base wherein the shield covers the teeth when the upper base is placed in the mouth.

15. The system of claim 13 further comprising:
    a shield extending from the concave portion of the upper base or the lower base wherein the shield covers the teeth when the first dental appliance and the second dental appliance are placed within the mouth.

16. The system of claim 13 further comprising:
    an occlusal surface on the first dental appliance wherein the occlusal surface contacts the upper teeth when the first dental appliance is placed within the mouth wherein the occlusal surface is flat.

17. The system of claim 13 wherein the interior surface is roughened.

18. The system of claim 13 further comprising:
    a socket formed within the first dental appliance wherein the socket is shaped to receive at least one of the teeth of the user.

19. The system of claim 13 wherein the upper base rotates with respect to the lower base via the hinge wherein the front end of the upper base is separable from the front end of the lower base via the hinge.

20. The system of claim 13 wherein the first dental appliance and the second dental appliance are sized to contact at least one but not all of the teeth when the first dental appliance and the second dental appliance are placed within the mouth.

21. The system of claim 13 further comprising:
a substance located between one tooth of the user and the concave portion wherein the substance enables the concave portion to adhere to one tooth of the user.

22. The system of claim 13 further comprising:
lingual tabs formed within the second dental appliance wherein the lingual tabs extend rearward into the mouth when the second dental appliance is placed within the mouth.

23. A dental appliance having a length defined between a first end and a second end wherein the dental appliance is placed within a mouth of a user having upper teeth and lower teeth wherein the mouth of the user has an incisor and a molar, the dental appliance comprising:
a generally U-shaped upper base having a front portion, a rear portion which is located opposite to the front portion and an upper occlusal surface wherein the upper occlusal surface contacts the upper teeth;
a generally U-shaped lower base having a front portion and a rear portion which is located opposite to the front portion wherein the lower base is connected to the upper base wherein the lower base has a lower occlusal surface wherein the lower occlusal surface contacts the lower teeth wherein the upper occlusal surface and the lower occlusal surface are sized to receive the upper teeth or the lower teeth of the user wherein the upper base and the lower base are made of a first material and a second material wherein the first material is stiffer than the second material wherein the second material moves one of the upper teeth of the user or one of the lower teeth of the user wherein the front portion of the upper base and the lower base is adjacent to the second material and the incisor in the mouth of the user and further wherein the rear portion of the upper base and the lower base is adjacent to the first material and the molar in the mouth of the user; and
a hinge insertable within the upper base and the lower base wherein the hinge connects the first end of the upper base and the first end of the lower base wherein the hinge and the first material of the upper base and the lower base attach the upper base and the lower base to the mouth of the user.

24. The dental appliance of claim 23 wherein the upper base is sized to contact teeth closest to an exterior of the mouth but does not contact teeth furthest within the mouth.

25. The dental appliance of claim 23 further comprising:
a plurality of sockets within the upper base wherein each of the sockets are sized to receive a single tooth of the user.

26. The dental appliance of claim 23 wherein the occlusal surface is flat.

27. The dental appliance of claim 23 further comprising:
a shield extending from the upper base wherein the reline material is adjacent to the shield.

28. The dental appliance of claim 23 further comprising:
a mark on the upper base indicating an amount of a reline material in contact with the upper base wherein the upper base receives the reline material wherein the reline material prevents the upper base from dislodging from the upper teeth of the user when the upper base is worn on the upper teeth.

29. The dental appliance of claim 23 further comprising:
a socket formed within the upper base wherein the socket is shaped to receive two or more of the teeth of the user.

30. The dental appliance of claim 23 further comprising:
a shield extending from the lower base wherein the shield covers the teeth when the lower base is placed in the mouth.

31. The dental appliance of claim 23 wherein the upper occlusal surface adheres to the upper teeth.

32. The dental appliance of claim 23 wherein
the lower base decreases in rigidity from the first end to the second end.

33. The dental appliance of claim 23 further comprising:
lingual tabs integrally formed with the lower base wherein the lingual tabs extend rearward into the mouth when the lower base is placed within the mouth.

34. The dental appliance of claim 23 wherein the upper occlusal surface and the lower occlusal surface are roughened.

35. A dental appliance having a width defined between a first end and a second end wherein the dental appliance is placed in a mouth of a user having upper teeth and lower teeth, the dental appliance comprising:
a generally U-shaped upper base having an upper occlusal surface wherein the upper occlusal surface contacts the upper teeth wherein the upper base is made from a first material and a second material wherein the first material is stiffer than the second material;
a generally U-shaped lower base connected to the upper base wherein the lower base has a lower occlusal surface wherein the lower occlusal surface contacts the lower teeth wherein the lower base is made from the first material and the second material;
a hinge integrally formed with the upper base and the lower base wherein the hinge connects the upper base and the lower base wherein the upper occlusal surface adheres to one of the upper teeth via the first material of the upper base and further wherein the second material of the lower base moves one of the lower teeth.

36. The dental appliance of claim 35 further comprising:
a substance surrounding the upper occlusal surface and the lower occlusal surface.

37. The dental appliance of claim 35 further comprising:
a plurality of sockets wherein each of the plurality of sockets is shaped to receive a single tooth.

38. The dental appliance of claim 35 wherein the upper occlusal surface and the lower occlusal surface are flat.

39. The dental appliance of claim 35 wherein the upper occlusal surface is roughened.

40. The dental appliance of claim 35 wherein the lower occlusal surface is roughened.

41. The dental appliance of claim 35 wherein the upper base is sized to contact teeth adjacent an exterior of the mouth but does not contact teeth furthest within the mouth.

42. The dental appliance of claim 35 wherein the upper base varies in rigidity from an exterior of the mouth to an interior of the mouth when the upper base is placed within the mouth.

43. The dental appliance of claim 35 wherein the hinge causes the upper base to adhere to the upper teeth.

44. The dental appliance of claim 35 wherein the lower base varies in rigidity from an exterior of the mouth to an interior of the mouth when the upper base is placed within the mouth.

45. The dental appliance of claim 35 wherein the hinge provides resistance against movement of the upper base toward the lower base.

46. The dental appliance of claim 35 wherein the upper base rotates with respect to the lower base via the hinge wherein the upper occlusal surface separates from the lower occlusal surface.

47. A method for treating a malocclusion of a user having a mouth having one or more teeth, the method comprising the steps of:
diagnosing the user with the malocclusion;
determining an amount of time the user is required to place the dental appliance within the mouth on a periodic basis wherein the dental appliance has a generally U-shaped base wherein the base is made from a first material and a second material wherein the first material is stiffer than the second material wherein the base has an upper occlusal surface and a lower occlusal surface which is located opposite to the upper occlusal surface wherein the upper occlusal surface and the lower occlusal surface have sockets formed within the base sized to receive at least one or more teeth of the user wherein a socket which is formed in the second material moves at least one of the teeth of the user and corrects the malocclusion; and
wearing the dental appliance for less than the amount of time required while extending the periodic basis.

48. The method of claim 47 further comprising the step of:
adhering the dental appliance to at least one of the teeth of the user to prevent the dental appliance from slipping within the mouth when the dental appliance is placed within the mouth.

49. The method of claim 47 further comprising the step of:
providing a second dental appliance after the malocclusion is treated wherein the second dental appliance acts as a retainer.

50. A dental appliance having a length defined between a first end and a second end wherein the dental appliance is placed within a mouth of a user having upper teeth and lower teeth wherein the mouth of the user has an incisor and a molar, the dental appliance comprising:
a generally U-shaped upper base having a front portion, a rear portion and an upper occlusal surface wherein the upper occlusal surface contacts the upper teeth;
a generally U-shaped lower base having a front portion and a rear portion which is located opposite to the front portion wherein the lower base is connected to the upper base wherein the lower base has a lower occlusal surface wherein the lower occlusal surface contacts the lower teeth wherein the front portion of the upper base and the lower base is made from a first material and the rear portion of the upper base and the lower base is made from a second material wherein the first material is stiffer than the second material wherein the front portion of the upper base and the lower base are adjacent to the incisor in the mouth of the user when the upper base and the lower base are worn in the mouth of the user wherein the rear portion of the upper base and the lower base are adjacent to the molar in the mouth of the user when the upper base and the lower base are worn in the mouth of the user; and
a hinging mechanism insertable within the upper base and the lower base wherein the hinging mechanism connects the upper base and the lower base wherein the upper occlusal surface and the lower occlusal surface are roughened.

51. The dental appliance of claim 50 further comprising:
a slot formed within the upper occlusal surface wherein the slot is sized to receive two or more teeth.

52. The dental appliance of claim 50 further comprising:
a slot formed within the lower occlusal surface wherein the slot is sized to receive two or more teeth.

53. The dental appliance of claim 50 further comprising:
lingual tabs formed within the lower base wherein the lingual tabs extend rearward into the mouth when the lower base is placed within the mouth.

54. The dental appliance of claim 50 further comprising:
a socket formed in the upper occlusal surface and the lower occlusal surface wherein the socket is sized to receive one of the teeth of the user.

55. The dental appliance of claim 50 wherein the lower base increases in rigidity from the first end to the second end.

56. The dental appliance of claim 50 wherein the upper base increases in rigidity from the first end to the second end.

57. A dental appliance having a width defined between a first end and a second end wherein the dental appliance is placed in a mouth of a user having upper teeth and lower teeth, the dental appliance comprising:
a generally U-shaped upper base having an upper occlusal surface wherein the upper occlusal surface contacts the upper teeth;
a generally U-shaped lower base connected to the upper base wherein the lower base has a lower occlusal surface wherein the lower occlusal surface contacts the lower teeth wherein the upper base and the lower base are made from a first material and a second material; and
a hinge integrally formed with the upper base and the lower base wherein the hinge connects the upper base and the lower base wherein the hinge provides resistance against movement of the upper base toward the lower base wherein the hinge prevents the upper base and the lower base from sliding when placed within the mouth of the user wherein the hinge and the first material of the upper base and the lower base attach the lower base and the upper base to the mouth of the user.

58. The dental appliance of claim 57 further comprising:
one or more sockets within the upper base wherein at least one of the sockets is shaped to correspond to a shape of one of the teeth.

59. The dental appliance of claim 57 further comprising:
one or more sockets within the lower base wherein at least one of the sockets is shaped to correspond to a shape of one of the teeth.

60. The dental appliance of claim 57 wherein the hinge is more rigid than the upper base and the lower base.

61. The dental appliance of claim 57 further comprising:
a mark on the lower base indicating an amount of a reline material in contact with the lower base wherein the lower base receives the reline material wherein the reline material prevents the lower base from dislodging from the lower teeth of the user when the lower base is worn on the lower teeth of the user.

62. The dental appliance of claim 57 wherein the upper base and the lower base are sized to contact at least one tooth but not all teeth when the upper base and the lower base are placed within the mouth.

63. A dental appliance which is placed in a mouth of a user having upper teeth and lower teeth to treat a malocclusion of the upper teeth, the dental appliance comprising;
a generally U-shaped base having a top side and a bottom side which is located opposite to the top side wherein an occlusal surface is formed on the top side of the base to receive the upper teeth wherein the occlusal surface treats the malocclusion wherein the malocclusion is associated only with the upper teeth wherein the base is made of a first material and a second material wherein the first material is stiffer than the second material wherein the base is attachable to at least one of the upper teeth of the user via the first material wherein the second material moves at least one of the upper teeth of the user; and two or more sockets formed within the top side of the base wherein at least one of the sockets is preformed and at least one of the sockets is customized to a shape of one of the upper teeth wherein the bottom side of the base does not contact the bottom teeth of the user when the base is worn in the mouth of the user.

64. The dental appliance of claim 63 further comprising:
a substance on the base wherein the substance prevents the base from slipping within the mouth of the user.

65. The dental appliance of claim 63 further comprising:
a hinge attached to the base wherein the hinge is made from the first material wherein the hinge separates the base and the lower teeth of the user when the base is worn in the mouth of the user.

66. The dental appliance of claim 63 further comprising:
a shield extending from the upper base wherein the shield covers the teeth when the upper base is placed in the mouth.

67. The dental appliance of claim 63 further comprising:
a slot formed along the base wherein the slot has a flat occlusal surface.

68. The dental appliance of claim 63 wherein at least one of the preformed sockets is sized to receive two or more of the teeth.

69. A dental appliance which is placed in a mouth of a user having lower teeth and upper teeth to treat a malocclusion of the lower teeth, the dental appliance comprising:
a generally U-shaped base having a top side and a bottom side which is located opposite the top side wherein an occlusal surface is formed on the bottom side of the base wherein the bottom side of the base is sized to receive the lower teeth wherein the occlusal surface treats the malocclusion wherein the malocclusion is associated only with the lower teeth wherein the base is made of a first material and a second material wherein the first material is stiffer than the second material wherein the second material of the base moves at least one of the lower teeth of the user;

two or more sockets formed within the bottom side of the base wherein at least one of the sockets is preformed and at least one of the sockets is customized to a shape of one of the lower teeth wherein the top side of the base does not contact the top teeth of the user when the base is worn in the mouth of the user.

70. The dental appliance of claim 69 wherein the first material of the base prevents the base from slipping within the mouth of the user.

71. The dental appliance of claim 69 further comprising:
a hinge attached to the base wherein the hinge is made from the first material wherein the hinge separates the base and the upper teeth of the user when the base is worn in the mouth of the user.

72. The dental appliance of claim 69 further comprising:
a shield extending from the upper base wherein the shield covers the teeth when the upper base is placed in the mouth.

73. The dental appliance of claim 69 further comprising:
a slot formed along the base wherein the slot has a flat occlusal surface.

74. The dental appliance of claim 69 wherein at least one of the preformed sockets is sized to receive two or more of the teeth.

* * * * *